United States Patent [19]

Nakano et al.

[11] Patent Number: 5,621,019

[45] Date of Patent: Apr. 15, 1997

[54] MONOMER HAVING VINYL GROUP, POLYMER THEREOF AND PHOTOSENSITIVE RESIN INCLUDING THOSE

[75] Inventors: Kaichiro Nakano; Shigeyuki Iwasa; Etsuo Hasegawa, all of Tokyo, Japan

[73] Assignee: NEC Corporation, Tokyo, Japan

[21] Appl. No.: 380,994

[22] Filed: Jan. 31, 1995

[30] Foreign Application Priority Data

Jan. 31, 1994 [JP] Japan .................................. 6-009030
Nov. 15, 1994 [JP] Japan .................................. 6-280695

[51] Int. Cl.$^6$ .............................. C08F 2/48; C08J 3/20; C08J 3/28
[52] U.S. Cl. ............................... 522/49; 522/50; 522/154
[58] Field of Search .......................... 525/353; 522/49, 522/50, 154

[56] References Cited

U.S. PATENT DOCUMENTS 5,217,491  6/1993  Vanderbilt .................................. 623/6
5,304,456  4/1994  Ueda et al. ............................... 525/497

FOREIGN PATENT DOCUMENTS 2-27660   6/1990   Japan .
5-134416  5/1993   Japan .
5-265212  10/1993  Japan .

OTHER PUBLICATIONS

"Applications of Photoinitiators to the Design of Resists for Semiconductor Manufacturing," Hiroshi Ito et al., American Chemical Society, Symp. Ser. vol. 242, 1984, pp. 11–23.
"ArF Excimer Laser Lithography (3)—Evaluation of Resist," Sasago et al., 35th Applied Physics Institution Conference Manuscripts, 1p–K–4, 1989, p. 9.
"Alicyclic Polymer for ArF and KrF Excimer Resist Based on Chemical Amplification," Takechi et al., Journal of Photopolymer Science and Technology, vol. 5, No. 3, 1992, pp. 439–445.

"Challenges in Excimer Laser Lithography for 256M DRAM and Beyond," Endo et al., IEDM Technical Digest, 1992, pp. 45–48.
"Poly(p–tert–butoxycarbonyloxystyrene): a, Convenient Precursor to p–hydroxystyrene Resins," Fréchet et al., Polymer, vol. 24, Aug. 1983, pp. 995–1000.
"A New Preparation of Triarylsulfonium and –selenonium Salts via the Copper (II)–Catalyzed Arylation of Sulfides and Selenides with Diaryliodonium Salts," Crivello et al. J. Org. Chem., vol. 43, No. 15, 1978, pp. 3055–3058.
"Chemically Amplified Resists: a Lithographic Comparison of Acid Generating Species," T. X. Neenan et al., SPIE, vol. 1086, Advances in Resist Technology and Processing VI 1989, pp. 2–10.
"Chemical Amplification Positive Resist Systems Using Novel Sulfonates as Acid Generators," Ueno et al., Procedings of PME '89, 1990, pp. 413–424.

(List continued on next page.)

*Primary Examiner*—Joseph L. Schofer
*Assistant Examiner*—Wu C. Cheng
*Attorney, Agent, or Firm*—Popham Haik Schnobrich & Kaufman, Ltd.

[57] ABSTRACT

The present invention presents a monomer including a vinyl group, which monomer is represented by a general formula (I) wherein $R_1$ represents one of a hydrogen atom, a tert-butoxycarbonyl group, a tetrahydropyran-2-yl group, a tetrahydrofuran-2-yl group, a 4-methoxytehydropyranyl group, a 1-ethoxyethyl group, a 1-butoxyethyl group and a 1-propoxyethyl group, $R_2$ represents a hydrocarbon residue including a bridged hydrocarbon group and having a carbon number ranging from 7 to 12 both inclusive, and $R_3$ represents one of a hydrogen atom and a methyl group.

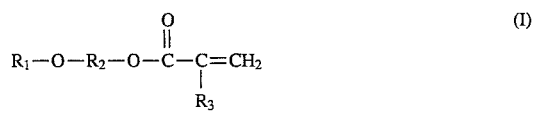

11 Claims, 1 Drawing Sheet

OTHER PUBLICATIONS

"Raney–Nickel–Isomerisierungen von Bicyclo[2.2.1] heptandiolen," Kurt Heyns et al., Chem. Ber. 105, 1972, pp. 1019–1027.

"Increased Electron Demand in the Solvolysis of Secondary 2–Norbornyl Tosylates," Lambert et al., Journal of the American Chemical Society, vol. 100, 1978, pp. 2501–2505.

"Positive, Chemically Amplified Aromatic Methacrylate Resist Employing the Tetrahydropyranyl Protecting Group," Taylor et al., Chem. Mater., vol. 3(6), 1991, pp. 1031–1040.

MONOMER HAVING VINYL GROUP, POLYMER THEREOF AND PHOTOSENSITIVE RESIN INCLUDING THOSE

BACKGROUND OF THE INVENTION

1. Field of the Invention

The invention relates to a monomer including a vinyl group and a polymer thereof, and further to a resin suitable for synthesizing a photosensitive resin to be exposed to far ultraviolet radiation (FUV) having a wavelength equal to or smaller than 220 nm as an exposure light.

2. Description of the Related Art

In a field of manufacturing various electronic devices such as VLSI which require minute processing in a submicron order, an electric device is now required to be more highly densifted and integrated. Thus, an improved lithography technique is required for forming a more minute pattern on a substrate.

In one known method for forming a minute pattern an exposure light having a shorter wavelength is used for forming a pattern of resist. This method is based on Rayleigh's formula representing a resolution R or a line width of an optical system. The Rayleigh's formula is as follows.

$$R = k\lambda/NA$$

wherein $\lambda$ represents a wavelength of an exposure light, NA is a numerical aperture of a lens, and k is a process factor. It can be understood from the Rayleigh's formula that a wavelength $\lambda$ of an exposure light is required to be shorter in order to accomplish a higher resolution or obtain a smaller R.

For instance, i-line which has a wavelength of 365 nm and is irradiated from a high-pressure mercury vapor lamp has been used as a light source for manufacturing a dynamic random access memory (DRAM) having an integration equal to or smaller than 64M bits. It is now being studied that as an exposure light source the i-line be replaced with KrF excimer laser having a shorter wavelength than the i-line, more specifically, having a wavelength of 248 nm in mass production process of 256M bits DRAM which requires a processing dimension to be smaller than 0.25 µm. It is also being studied presently to use a light source having a shorter wavelength for the purpose of manufacturing DRAM having an integration higher than 1 G bit which requires a processing dimension to be smaller than 0.2 µm. For that purpose, an excimer laser such as KrCl having a wavelength of 222 nm, ArF having a wavelength of 193 nm and $F_2$ having a wavelength of 157 nm is considered to be useful according to the book "Materials and Processes for Deep UV Lithography" authored by Takumi Ueno, Takao Iwayanagi, Saburo Nonogaki, Hiroshi Ito and C. Grant Wilson, 1988, published through Bunshin Shuppan.

However, in view of both a target yield of mass production, in other words, a period of time to be taken for an exposure step, and an economical efficiency to be obtained when a novel light source is to be used in manufacturing, photolithography technique is considered to be more useful than a method of exposing with electron beam and a method of exposing with X-ray, because the photolithography technique can expose all objects to light at a time and a lot of experiences about the photolithography technique have been accumulated. Thus, there is required to develop the photolithography technique which uses a light having a shorter wavelength than KrF excimer laser, that is, a light having a wavelength equal to or shorter than 220 nm for manufacturing LSI having an integration greater than 1 G bits.

Using excimer laser as a light source presents many problems to be solved including that the lifetime of gas from which a laser is to be irradiated is short and that a laser irradiation apparatus is expensive. Thus, when an excimer laser is to be used as a light source in mass production of electronic devices, it is necessary to improve cost performance of the laser. Accordingly, resist material for minute processing is required to have a high sensitivity as well as to have a high resolution in response to more minute processing dimensions.

One known method for enhancing a sensitivity of resist is a chemically amplified resist which utilizes a photo acid generator as a sensitizer. For instance, Japanese examined Patent Public Disclosure No. 2-27660 has suggested a resist comprising a combination of triphenylsulfonium hexafluoroarsenate and poly(p-tert-butoxycarbonyloxystyrene-co-α-methylstyrene). There are many reports about a chemically amplified resist for use with KrF excimer laser, for instance, in American Chemical Society Symposium Series, 1984, Vol. 242, pages 11–23, reported by Hiroshi Ito and C. Grant Willson. A chemically amplified resist is characterized by the steps of transferring proton acid, which is generated by a photo acid generator which is one of constituents of the resist, through a resist solid phase by means of post-exposure heat treatment, and amplifying chemical reaction of a resist resin up to hundreds of to thousands of times due to the proton acid in a way like catalytic action. Thus, a quite higher sensitivity can be obtained relative to prior resist which has an optical reaction efficiency, which is defined as a reaction per a photon, smaller than one (1).

Presently, most of newly developed resist is a chemical amplified resist, and hence a chemical amplification system has to be adopted in development of a highly sensitive material in response to a shorter wavelength of an exposure light source.

In a lithography technique in which there is to be used an excimer laser having a wavelength shorter than 220 nm as an exposure light, a resist for forming a minute pattern is required to have new characteristics which prior resist did not have.

The above mentioned new characteristics with respect to constituents of a resin are (a) high transparency to exposure lights having a wavelength smaller than 220 nm, and (b) etching-resistance, and with respect to a photosensitizer or a photo acid generator are (a) high transparency to exposure lights having a wavelength smaller than 220 nm, and (b) high reaction efficiency or high photo acid generation ability to such exposure lights.

In conventional lithography in which there is used an exposure light having a wavelength longer than that of KrF excimer laser (248 nm), a photosensitive resin includes a resin which has aromatic rings in a unit structure, such as novolac resin and poly(p-vinylphenol). The dry etching resistance of such aromatic rings gives a dry etching resistance to the above mentioned resin. However, the aromatic rings quite intensively absorb lights having a wavelength equal to or shorter than 220 nm, and hence the above mentioned conventional resin cannot be applied to an exposure light having a wavelength shorter than 220 nm. Specifically, most exposure lights are absorbed at a surface of a resist, and accordingly cannot reach a substrate with the result that a minute resist pattern cannot be formed. Such a fact has been reported, for instance, in "ArF excimer laser lithography (3)—Evaluation of Resist—", the 35th Applied Physics Institution Conference Manuscripts, 1989, 1p-K-4 by Sasago et al. Thus, there is a demand of resin materials which do not include aromatic rings but have a dry etching resistance.

When an exposure light having a wavelength shorter than 220 nm is to be used, a light transparency to an exposure light of a photosensitizer or a photo add generator is quite important as well as a resin material. It is not allowed to use a conventional photo add generator such as triphenylsulfonium hexafluoroarsenate disclosed in Japanese examined Patent Public Disclosure No. 2-27660, because it has aromatic rings. The inventors has already developed a novel photo add generator satisfying the above mentioned conditions and has filed as Japanese Patent Applications Nos. 5-174528 and 5-174532.

For instance, there has been reported a copolymer having an adamantylmethacrylate unit which is an alicyclic polymer, as a polymer having a transparency, to a tight having a wavelength of 193 nm and further having dry-etching resistance, in Journal of Photopolymer Science and Technology, 1992, Vol. 5, No. 3, pages 439–446, by Takechi et al. and Japanese Unexamined Patent Public Disclosure No. 5-265212. For another instance, a polymer of poly(norbonyl-methacrylate) has been reported as a polymer having a transparency to a light having a wavelength of 193 nm and further being dry-etching resistant, in, 1992, IEDM Technical Digest, pages 45–48, by M. Endo et al.

However, the former resins do not have a residue in an adamantane residue unit, which resin is capable of indicating a difference of solubility between pre-exposure and post-exposure. Accordingly, those resins can be used as resin constituent of a resist only when they are copolymerized with a comonomer capable of indicating a difference in solubility, such as tetrahydropyranylmethacrylate. However, since a content ratio of comonomer is required to be approximately 50 mol % and a comonomer unit has quite low dry etching resistance, the dry etching resistance of the resin is remarkably deteriorated with the result that the above mentioned resins are not practical as dry etching resistant resin. In addition, these polymers having an alicyclic alkyl group tend to have a high hydrophobic property because an alicyclic group and a protection group (a polarity converting group) both present in a polymer compound are hydrophobic. Consequently, a thin film composed of these polymers has a weak adhesion with a silicon substrate, and hence it was quite difficult to repeat the formation of uniform films by applying those polymers to a silicon substrate. In other words, those copolymers do not include polarity section unlike a novolac resin having been widely used in a resist, and hence have only a weak adhesion with a silicon substrate. Furthermore, those copolymers have a low solubility to alkaline developing aqueous solution, and hence can have only a low sensitivity. In addition, those copolymers are accompanied by a problem that a lot of scum is prone to be generated after development.

SUMMARY OF THE INVENTION

Thus, there is demanded a resin to be used as resin material, which resin has a high transparency to a light having a wavelength equal to or shorter than 220 nm, a high dry etching resistance, a functional group capable of indicating a difference in solubility between pre-exposure and post-exposure, and an enhanced adhesion with a substrate. It is an object of the invention to provide a solution to such demand.

The inventors have discovered that the above mentioned problems can be solved by a novel compound and polymer thereof both of which will be explained hereinbelow in detail. The invention is based on such discovery.

Namely, the inventors have found that the above mentioned problems can be solved by introducing a bridged hydrocarbon residue to a resin for providing the resin with a high transparency to a light having a wavelength equal to or shorter than 220 nm and a high dry etching resistance, and further by introducing into the resin a hydroxyl group bonded to a bridged hydrocarbon group as a polarity group and polarity converting section residue.

The invention provides a novel monomer including a vinyl group, represented by a general formula (I), below, wherein $R_1$ represents one of a hydrogen atom, a tert-butoxycarbonyl group, a tetrahydropyran-2-yl group, a tetrahydrofuran-2-yl group, a 4-methoxytetrahydropyranyl group, a 1-ethoxyethyl group, a 1-butoxyethyl group and a 1-propoxyethyl group, $R_2$ represents a hydrocarbon residue including a bridged hydrocarbon group and having a carbon number ranging from 7 to 12 both inclusive, and $R_3$ represents one of a hydrogen atom and a methyl group.

The invention further provides a novel polymer introduced from the above mentioned monomer and represented by a hereinbelow indicated general formula ((II) wherein $R_1$ and $R_6$ represent one of a hydrogen atom, a tert-butoxycarbonyl group, a tetrahydropyran-2-yl group, a tetrahydrofuran-2-yl group, a 4-methoxytetrahydropyranyl group, a 1-ethoxyethyl group, a 1-butoxyethyl group and a 1-propoxymethyl group, $R_2$ and $R_4$ each represents a hydrocarbon residue including a bridged hydrocarbon group and having a carbon number ranging from 7 to 12 both inclusive, $R_3$, $R_5$, $R_7$ and $R_8$ each represents one of a hydrogen atom and a methyl group, "a" is a variable ranging from 0 to 0.9 both inclusive, "b" is a variable ranging from 0 to 0.9 both inclusive, "c" is a variable ranging from 0 to 0.7 both inclusive, and "d" is a variable ranging from 0 to 0.5 both inclusive, a sum of "a", "b", "c" and "d" is one (a+b+c+d=1), both "a" and "b" can not be equal to zero (0), and n represents a positive integer ranging from 10 to 500 both inclusive.

In the above mentioned polymer, $R_2$ and $R_4$ each represents a hydrocarbon residue including a bridged hydrocarbon group and having a carbon number ranging from 7 to 12 both inclusive, and preferably represents an aliphatic hydrocarbon residue including a bridged hydrocarbon group and having a carbon number ranging from 7 to 12 both inclusive. In the general formula (II), $R_2$ may be identical to $R_4$ or different from $R_4$, and similarly, $R_3$ $R_5$, $R_7$ and $R_8$ may be identical to or different from one another. Specifically, $R_3$, $R_5$, $R_7$ and $R_8$ are selected from a tricyclo[5.2.1.0$^{2.6}$]decane-4,8-dimethylene group, a norbornane-2,6-dimethylene group, a tricyclo[5.2.1.0$^{2.6}$]decanediyl group, an adamantanediyl group, a norbornane-2,3-diyl group, a norbornene-2,2-dimethylene group, a norbornane-2,3-dimethylene group, a norbornane-2,5-dimethylene group, and a bicycle [2.2.2]octene-2,3-dimethylene group.

| $R_2$, $R_4$ | Chemical constitution formula of the group |
|---|---|
| tricyclo [5.2.1.0$^{2.6}$] decanedimethylene group | |
| tricyclo [5.2.1.0$^{2.6}$] decanediyl group | |
| norbornanediyl group | |
| norbornanedimethyl group | |
| adamantanediyl group | |

The polymer in accordance with the invention has a high transparency in the band of far ultraviolet radiation (FUV) having a wavelength shorter than 220 nm, and can contain a residue having a group unstable to an acid, at a desired ratio.

A monomer including a vinyl group represented by the general formula (I) can be synthesized, for instance, by the following method. First, a diol compound indicated by general formula (III) is prepared wherein $R_2$ is the same as that in the general formula (I) or (II).

$$HO-R_2-OH \qquad (III)$$

The $R_2$ group may be selected from a tricyclo[5.2.1.0$^{2.6}$] decane-4,8-dimethanol group, a norbornane-2,6-dimethanol group, a tricycto [5.2.1.0$^{2.6}$]decanediol group, an adamantane-diol group, a norbornane-2,3-diol group, a norbornane-2,2-dimethanol group, a norbornane-2,3-dimethanol group, a norbornane-2,5-dimethanol group, a bicycle[2.2.2]octene-2,3-dimethanol group, an isobornanediol group or an isobornanedimethanol group. Then, diol compound is subject to reaction with methacryoylchloride or acryoylchloride having an equal mol with the diol compound, for 1 to 10 hours in a solvent of, for instance, dehydrotetrahydrofuran or methylene chloride under the presence of triethylamine or pyridine. Thereafter, the reacted diol compound is refined in a conventional manner to thereby synthesize an intermediate product, namely, monomethacrylatemonool derivatives or monoacrylatemonool derivatives, both of which correspond to compound to be produced when $R_1$ is a hydrogen atom in the general formula (I). Thus produced intermediate product is processed as follows.

The monomer including a vinyl group, indicated by the general formula (I) wherein $R_1$ is a tert-butoxycarbonyl group can be synthesized by reacting a hydroxyl group of the above mentioned intermediate product to be obtained when a hydrogen atom is selected as $R_1$ in the general formula (I), with dicarbonic acid di-tert-butyl in a solvent of dehydrotetrahydrofuran under the presence of potassium-tert-butoxide at an ambient temperature through 50 degrees centigrade for 3 to 24 hours in a conventional method such as suggested by J. M. Frechet in Polymer Vol. 24, No. 8, 1983, pages 995–1000.

The monomer including a vinyl group, indicated by the general formula (I) wherein $R_1$ is one of tetrahydropyran-2-yl group and tetrahydrofuran-2-yl group can be synthesized as follows, for instance. First, diol compound indicated by the general formula (III) is reacted with 3,4-dihydro-2H-pyran under a small amount of acidic catalyst such as concentrated sulfuric acid at a temperature ranging from 30 to 80 degrees centigrade for 15 to 24 hours, to thereby produce monotetrahydropyran-2-yl derivative having a general formula (III). Then, the thus produced derivative is reacted with methacryoyl chloride having an equal mol to that of the derivative, in a dehydromethylene chloride solvent under excessive base, for instance, base having a mol more than twice, preferably more than five times, relative to a mol of the derivative, at a temperature of ice cooling temperature to 50 degrees centigrade for 1 to 20 hours, to thereby obtain a monomer including a vinyl group, indicated by the general formula (I) wherein $R_1$ is a tetrahydropyran-2-yl group. A monomer including a vinyl group, indicated by the general formula (I) wherein R1 is a tetrahydrofuran-2-yl group can be synthesized in the same way as above mentioned using 2,3-dihydrofuran in place of 3,4-dihydro-2H-pyran.

Furthermore, a homopolymer corresponding to a polymer to be obtained when a=1 in the general formula (II) can be produced by homopolymerization of a monomer indicated by the general formula (I).

A copolymer indicated by the general formula (II) can be obtained by suitably selecting polymerization conditions such as a mixture ratio of a monomer A indicated by the general formula (I) in which $R_1$ is a tert-butoxycarbonyl group and a monomer B indicated by the general formula (I) in which $R_1$ is a hydrogen atom. The thus obtained copolymer has a desired value of "a".

The polymerization reaction of a monomer indicated by the general formula (I) is carried out by adding thereto free-radical initiator such as azo-bisisobutyronitrile in a tetrahydrofuran solvent under an atmosphere of an inert gas such as argon (Ar) and nitrogen ($N_2$) at a mixture ratio of the monomer to the initiator being in the range of 10 to 200, and heating and stirring the mixture at a temperature ranging from 50 to 70 degrees centigrade for 0.5 to 10 hours.

The degree of polymerization of a polymer in accordance with the invention, indicated by n in the general formula (II), ranges from 10 to 500 both inclusive, preferably from 10 to 200 both inclusive.

A thin film composed of a polymer indicated by the general formula (II) and having a thickness of 1.0 μm has a high transmittance to ArF excimer laser beam having a wavelength of 193 nm. Specifically, such a thin film has a transmittance in the range from 65 to 75%. This shows that the polymer is practical in use.

A thin film composed of a polymer indicated by the general formula (II) wherein $R_1$ is a hydrogen atom, $R_3$ is a methyl group and $R_2$ is a tri-cyclo[$5.2.1.0^{2 \cdot 6}$]decane-dimethyl, "a" is equal to one (1), and "b", "c" and "d" are zero (0), has an etching speed of approximately 180 angstroms per minute in $CF_4$ gas reaction ion etching. This speed is equivalent to that of poly (p-vinylphenol) thin film.

It was also confirmed that this homopolymer has a high adhesion to a silicon substrate.

The invention provides a photosensitive resin comprising a resin and a photo acid generator. The resin includes a polymer represented by the general formula (II) wherein $R_1$ and $R_6$ represent one of a hydrogen atom, a tert-butoxycarbonyl group, a tetrahydropyran-2-yl group, a tetrahydrofuran-2-yl group, a 4-methoxytetrahydropyranyl group, a 1-ethoxyethyl group, a 1-butoxyethyl group and a 1-propoxymethyl group, $R_2$ and $R_4$ each represents a hydrocarbon residue including a bridged hydrocarbon group and having a carbon number ranging from 7 to 12 both inclusive, $R_3$, $R_5$, $R_7$ and $R_8$ each represents one of a hydrogen atom and a methyl group, "a" is a variable ranging from 0 to 0.9 both inclusive, "b" is a variable ranging from 0 to 0.9 both inclusive, "c" is a variable ranging from 0 to 0.7 both inclusive, and "d" is a variable ranging from 0 to 0.5 both inclusive, a sum of "a", "b", "c" and "d" is one (a+b+c+d=1), both "a" and "b" can not be equal to zero (0), and n represents a positive integer ranging from 10 to 500 both inclusive.

Photo acid generators usable in the photosensitive resin may be selected, for instance, from any one of (a) triphenylsulfonium salt derivatives disclosed in Journal of the Organic Chemistry, 1978, Vol. 43, No. 15, pages 3055–3058, by J. V. Crivello, (b) onium salts such as sulfonium salt, iodonium salt, diazonium salt and ammonium salt, (c) 2,6-dinitrobenzyl ester disclosed in SPIE Proceedings, 1989, Vol, 1086, pages 2–10, by T. X. Neenan et al., (d), 1,2,3-tri(methanesulfonyloxy)benzene shown in Proceedings of PME '89, 1990, pages 413–424, reported by Takumi Ueno et al. and published through Kodansha, (e) sulfosuccinimide disclosed in Japanese Patent Public Disclosure No. 5-134416, and (f) photo acid generators each indicated by following general formulas (IV) and (V) which have been suggested by the inventors in Japanese Patent Applications Nos. 5-174528 and 5-174532.

In the general formula (IV), $R_9$ and $R_{10}$ are one of straight-chain, branching and cyclic alkyl groups, and $R_{11}$ is one of straight-chain, branching and cyclic alkyl groups, a 2-oxocydic alkyl group, 2-oxostraight-chain and branching alkyl groups, and Y— represents a twin ion such as $BF_4$—, $AsF_6$—, $SbF_6$—, $PF_6$—, $CF_3COO$—, $ClO_4$— and $CF_3SO_3$—.

In the general formula (V), $R_{12}$ and $R_{13}$ are one of a hydrogen and straight-chain, branching and cyclic alkyl groups, and $R_{14}$ is one of a hydrogen, straight-chain, branch- In the photosensitive resin in accordance with the invention, the resin is included by weight percent in the range from 75 to 99.8 both inclusive, and the photo acid generator is included by weight percent in the range from 0.2 to 25 both inclusive.

The photosensitive resin in accordance with the invention basically includes a polymer, a photo acid generator and a solvent.

The photo acid generator generates an acid under a light having a wavelength equal to or less than 300 nm, more preferably 220 nm. In the invention, any photo acid generator may be used if a combination of the polymer and the photo acid generator is sufficiently soluble in an organic solvent, and further if it is possible to form a uniform layer composed of a solution of the photo acid generator by means of a layer forming process such as spin coating process. The photo acid generator may include a plurality of kinds of photo acid generators, and may be used in combination with photosensitizer.

ing and cyclic alkyl groups and a haloalkyl group such as perfluoroalkyl.

When an exposure light having a wavelength equal to or shorter than 220 nm is to be used, it is preferable to select a photo acid generator indicated by the general formula (IV) or (V) for enhancing light transmittance of a photosensitive resin. The photo add generator such as triphenylsulfonium trifluoromethanesulfonate (TPS) presently, widely used for KrF excimer laser lithography has a quite strong light-absorbing property in the range of far ultraviolet radiation (FUV) having a wavelength equal to or shorter than 220 nm, and hence it is required to limit an amount thereof if it is to be used as a photo acid generator in the invention. Now comparing a transmittance at a wavelength of 193.4 nm which is a main wavelength of ArF excimer laser beam, a transmittance of a film (1 μm thick) composed of a polymer indicated by the general formula (II) and containing TPS at 1.5% by weight on the basis of a total weight of the film is approximately 40%, and a transmittance of a film composed of a polymer indicated by the general formula (IV) and containing TPS at 5.5% by weight is approximately 6%. On the other hand, a transmittance of a poly(methylmethacrylate) film containing, for instance, cyclohexylmethyl(2-oxocyclohexyl)sulfonium trifluoromethanesulfonate, which is one of sulfonium salt derivatives shown with the formula (IV), at 5% by weight was 71%, and at 30% by weight was 55%, both of which were higher than the formerly mentioned transmittance. Thus, any of the photo acid generators shown with the formulas (IV) and (V) absorbs quite little amount of light in the band of FUV having a wavelength ranging from 185.5 nm to 220 nm, and accordingly it is obvious that they are preferable for a constituent of a resist to be used for ArF excimer laser lithography in terms of transparency to an exposure light. Specifically, a photo acid generator may be selected from any one of cyclohexylmethyl(2-oxocyclohexyl)sulfonium trifluoromethanesulfonate, dicyclohexyl(2-oxocyclohexyl)sulfonium trifluoromethanesulfonate, 2-cyclohexylsulfonylcyclohexanone, dimethyl(2-oxocyclohexyl)sulfonium trifluoromethanesulfonate, triphenylsulfonium trifluoromethanesulfonate, diphenyliodonium trifluoromethanesulfonate, and N-hydroxysuccinimide trifluoromethanesulfonate. However, it should be noted that a photo acid generator to be used in the invention is not to be limited to those, and any other photo acid generator may be selected.

A single kind of or a plurality of kinds of photo acid generator(s) may be used in the photosensitive resin in accordance with the invention. The photo acid generator is contained by weight percent preferably in the range from 0.2 to 25 both inclusive, and more preferably in the range from 1 to 15 both inclusive. If a content rate of the photo acid generator would be lower than 0.5% by weight, the photosensitive resin could have only quite a small sensitivity, and hence the formation of a pattern becomes difficult. On the other hand, if a content rate of the photo acid generator would be higher than 25% by weight, it would be difficult to form a uniform layer, and further there would be posed a problem that scum tends to be generated after development of a pattern. A content rate of the polymer is generally in the range from 75 to 99.8% by weight, and preferably in the range from 85 to 99% by weight on the basis of the total weight including the polymer itself.

Any organic solvent may be used in the invention, if a constituent thereof composed of polymer and alkylsulfonium salt and so on would be sufficiently soluble in a solvent, and if it would be possible to form a uniform layer from a solution by means of a method such as spin coating process. A single kind of solvent or a plurality of kinds of solvents in combination may be used. Specifically, a solvent to be used in the invention is selected from any one of n-propyl alcohol, isopropyl alcohol, n-butyl alcohol, tert-butyl alcohol, methylcellosolve acetate, ethylcellosolve acetate, propyleneglycol monoethylether acetate, methyl lactate, ethyl lactate, 2-methoxybutyl acetate, 2-ethoxyethyl acetate, pyrubic acid methyl, pyrubic acid ethyl, 3-methoxypropionatemethyl, 3-methoxypropionateethyl, N-methyl-2-pyrrolidinone, cyclohexanone, cyclopentanone, cyclohexanol, methylethylketone, 1,4-dioxan, ethyleneglycol, monomethylether, ethyleneglycol monomethylether acetate, ethyleneglycol monoethylether, ethyleneglycol monoisopropylether, diethyleneglycol monomethylether, and diethyleneglycol dimethylether. It should be noted that a solvent to be used in the invention is not to be limited to the above mentioned ones.

As having been explained, basic constituents of the photosensitive resin in accordance with the invention are the above mentioned alkyl-sulfonium salt compound, polymer and solvent. However, the photosensitive resin may include other constituents such as surfactant, pigment, stabilizer, reagent for enhancing application property, and dye.

A developing solution to be used when a minute pattern is to be formed may be selected from any one of an organic solvent to be selected in accordance with solubility of polymer to be used in the invention, a mixture solvent containing the above mentioned organic solvent, alkaline solution, alkaline aqueous solution or a mixture thereof each having a suitable concentration, and a mixture of the alkaline solution, organic compound and organic solvent. The organic solvent to be used in the invention may be selected from any one of (a) ketone such as acetone, methylethylketone, methylisobutylketone, cyclopentanone, cyclohexane, (b) alcohol such as methylalcohol, ethylalcohol, n-propylalcohol, isopropylalcohol, n-butylalcohol, isobutylalcohol, tert-butylalcohol, cyclopentanol, cyclohexanol, and (c) any other organic solvents such as tetrahydrofuran, dioxane, ethylacetate, butylacetate, isoamylacetate, benzene, toluene, xylene and phenol. The alkaline solution to be used may be selected from any one of (a) inorganic alkali such as sodium hydroxide, potassium hydroxide, sodium silicate, and ammonia, (b) organic amine such as ethyl amine, propyl amine, diethyl amine, dipropyl amine, trimethyl amine, and triethyl amine, (c) an aqueous solution or an organic solvent each containing organic ammonium salt such as tetramethylammonium hydroxide, tetraethylammonium hydroxide, trimethylhydroxyme thylammonium hydroxide, triethylhydroxymethylammonium hydroxide, and trimethylhydroxyethylarnmonium hydroxide, or a combination thereof.

A novel polymer obtained by polymerizing a monomer in accordance with the invention provides a novel monomer and polymer each including a hydroxyl group. The polymer in turn provides a resin material of which a resist is composed, having a high transparency to a light having a wavelength equal to or shorter than 220 nm, a high dry etching resistance, a functional group capable of a difference in solubility between pre-exposure and post-exposure, and an improved adhesion with a substrate. A photosensitive compound composed of the resin and a photo acid generator induces a remarkable change in solubility of the resist due to a breakdown of a protection group which protects a hydroxyl group, under the presence of proton acid as a catalyst, which proton acid is generated by being exposed to a light having a wavelength equal to or shorter than 220 nm.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained hereinbelow.

[Embodiment 1]: Synthesis of tricyclodecanedimethanol-monomethacrylate

Tricyclodecanedimethanolmonomethacrylate is represented by a general formula (VI) wherein X and Y indicate a hydrogen atom or a methacryloyl group, and X is not identical to Y.

(VI)

The followings was put into a 500 ml flask having four openings and equipped with a calcium chloride (CaCl$_2$) drying tube, an isotactic dropping funnel and a thermometer:
(a) 19.6 grams (100 mmol) of tricyclodecane-4,8-dimethanol commercially available from Aldrich Chemical Company, Inc. (U.S.A.) with the lot number; B4, 590-9
(b) 10.1 grams (100 mmol) of dry triethylamine; and
(c) 200 ml of dry tetrahydrofuran.

The mixture was stirred to make uniform solution, and then cooled in ice bath. While the solution was being stirred hard with a teflon bar, 50 ml of dry tetrahydrofuran into which 10.4 grams (100 mmol) of methacryloyl chloride, commercially available from Tokyo Kasei K.K.,had been dissolved was slowly dropped into the solution through a dropping funnel. After the dropping was completed, the resultant solution was stirred in ice bath for an hour, and then allowed to stand at an ambient temperature for ten hours. After the filtration of the deposit, the solvent was removed from the filtrate under reduced pressure. Then, the residue was dissolved in 500 ml of chloroform (CHCl$_3$). Then, the solution in which the residue was dissolved was disposed with 0.5N HCl, saturated salt aqueous solution, 3% sodium bicarbonate aqueous solution and saturated salt aqueous solution in this order. A chloroform layer was dehydrated with magnesium sulfate, and then was filtered. The residue which was obtained by removing the solvent by means of an evaporator was is refined with a silica gel column to thereby obtain 6.6 grams of a target material. The yield was 25%. IR was measured with an analyzer, IR-470 model available from Shimazu Seisakusho, and $^1$H-NMR was measured with an analyzer, AMX-400 model available from Bruker Instruments.

Elemental Analysis Value (Weight %) C: 72.4 (72.7) H: 9.5 (9.2)

The values in parentheses indicate calculation values calculated with C$_{16}$H$_{24}$O$_3$ whose MW is 264.366.

IR(cm$^{-1}$): 3350 ($v_{OH}$), 1720($v_{C=O}$), 1640($v_{C=C}$)

NMR (CDCl$_3$, internal standard material: tetramethylsilane) ppm: 0.9–2.1 (m, 17H), 3.2 (s, 2H), 3.9 (s, 2H), 5.6 (m, 1H), 6.1 (m, 1H)

[Embodiment 2]: Synthesis of tricyclodecanedimethanol-monoacrylate

Tricyclodecanedimethanolmonoacrylate is represented by a general formula (VII) wherein X and Y indicate a hydrogen atom or a acryloyl group, and X is not identical to Y.

(VII)

Similarly to the embodiment 1, tricyclodecanedimethanolmonoacrylate was synthesized using 9.1 grams (100 mmol) of acryloyl chloride in place of 10.4 grams (100 mmol) of methacryloyl chloride. There was obtained 5.0 grams of tricyclodecanedimethanolmonoacrylate. The yield was 20%.

Elemental Analysis Value (Weight %) C: 71.9 (72.0) H: 8.9 (8.9)

The values in parentheses indicate calculation values calculated with C$_{15}$H$_{22}$O$_3$ whose MW is 250.339.

IR(cm$^{-1}$): 3350 ($v_{OH}$), 1725($v_{C=O}$), 1630($v_{C=C}$)

NMR (CDCl$_3$, internal standard material: tetramethylsilane) ppm: 0.9–2.1 (m, 14H), 3.2 (s, 2H), 3.8 (s, 2H), 5.6–6.4 (m, 3H)

[Embodiment 3]: Synthesis of norbornanediol-monomethacrylate

Norbornanediolmonomethacrylate is represented by a general formula (VIII) wherein X and Y indicate a hydrogen atom or a methacryloyl group, and X is not identical to Y.

(VIII)

Similarly to the embodiment 1, norbornanediol methacrylate was synthesized using 12.8 grams (100 mmol) of norbornane-2,3-diol in place of 19.6 grams (100 mmol) of tricyclodecane-4,8-dimethanol according to a method suggested by K. Heyns et al. in Kemische Berichte, 1972, Vol. 105, page 1019, and also to a method suggested by J. B. Lambert in Journal of the American Chemical Society, Vol. 100, page 2501. There was obtained 3.5 grams of norbornanediol methacrylate. The yield was 18%.

Elemental Analysis Value (Weight %) C: 67.2 (67.3) H: 8.5 (8.2)

The values in parentheses indicate calculation values calculated with C$_{11}$H$_{16}$O$_3$ whose MW is 196.247.

IR(cm$^{-1}$): 3350 ($v_{OH}$), 1725($v_{C=O}$), 1630($v_{C=C}$)

NMR (CDCl$_3$, internal standard material: tetramethylsilane) ppm: 1.0–2.3 (m, 11H), 3.8 (m, 1H), 4.8 (m, 1H), 5.6 (m, 1H), 6.1 (m, 1H)

[Embodiment 4]: Synthesis of poly(tricyclodecanedimethanolmonomethacrylate)

Poly(tricyclodecanedimethanolmonomethacrylate) is represented by a general formula (IX) wherein Z indicates a tricyclodecane-4,8-diyl group, and m indicates a positive integer.

(IX)

In a 100 ml eggplant-shaped flask having three stop cocks and a cooling tube, 5.0 grams (18.9 mmol) of tricyclodecanedimethanolmonomethacrylate synthesized in the first embodiment was dissolved in 50 ml of dry tetrahydrofuran in argon (Ar) gas atmosphere. To the solution was added 0.164 grams (1.0 mmol) of 2,2'-azobis(isobutyronitrile), a polymerization initiator, and then the solution was heated at 60 degrees centigrade for 3 hours in an argon gas atmosphere. The resultant solution was cooled down to an ambient temperature, and then was introduced into 0.5 liter of ether. The gathered deposit was precipitated and refined once again with tetrahydrofuran/ether. The deposit of precipitated polymer was gathered by filtration, and then was dried at 40 degrees centigrade under 2 mmHg for 24 hours. Thus, there was obtained 3.5 grams of white-colored polymer powder. The yield was 70%. The polystyrene equivalent molecular weight was 9000. An analyzer was model LC-9A/ SPD-6A commercially available from Shimadzu Corporation, an analysis column was model GPCKF-80M commercially available from Showa Denko K.K., and a mobile phase was tetrahydrofuran.

Elemental Analysis Value (Weight %) C: 72.5 (72.7) H: 9.2 (9.2)

The values in parentheses indicate calculation values calculated with $(C_{16}H_{24}O_3)_n$ whose MW is 264.365.

IR(cm$^{-1}$): 3350 ($\nu_{OH}$), 1720($\nu_{C=O}$), $\nu_{C=C}$ The characteristics absorption band was eliminated.

[Embodiment 5]: Synthesis of partial tert-butoxycarbonyl-(BOC) polymer

Tert-butoxycarbonyl(BOC) polymer is represented by a general formula (X) wherein Z indicates a tricyclodecane-4,8-diyl group, and m indicates a positive integer.

(X)

In a 100 ml eggplant-shaped flask having a calcium chloride drying tube were put 2.64 grams (10 mmol) of the polymer having been synthesized in the embodiment 4 and 30 ml of dry tetrahydrofuran in argon (Ar) gas atmosphere. To the flask was also added 1.12 grams (10 mmol) of potassium tert-butoxide, and then the mixture was stirred with a teflon bar. To the mixture was further added a solution in which 2.18 grams (10 mmol) of dicarbonic add ditert-butyl was dissolved in 10 ml of dry tetrahydrofuran. Then, the resultant was stirred hard at an ambient temperature for 10 hours. Then, to the resultant solution was added 20 ml of ice and water, and after stirring further added 200 ml of chloroform. The thus obtained solution was rinsed. Then, an organic layer was dehydrated with magnesium sulfate, and then was filtrated. The solvent was removed from the filtration under reduced pressure. The residue was deposited and refined twice with chloroform/ether to thereby obtain a certain amount of solid. The solid was dried under 2 mmHg at 40 degrees centigrade for 24 hours to thereby obtain a target polymer by 2.8 grams.

IR: 3350 cm$^{-1}$ ($\nu_{OH}$), 1760 cm$^{-1}$ ($\nu_{C=O}$), 1720 cm$^{-1}$ ($\nu_{C=O}$)

Elemental Analysis Value (Weight %) C: 70.5 H: 9.1

The tert-butoxy-carbonyl(BOC) introduction rate (x) calculated based on the above mentioned elemental analysis results was 0.34.

[Embodiment 6]: Synthesis of tricyclodecanedimethanol monomethacrylate mono-tert-butylcarbonate Tert-butoxycarbonyloxymethyltricyclodecanemethanolmethacrylate is represented by a general formula (XI) wherein X and Y indicate a tert-butoxycarbonyl group or a methacryloyl group, and X is not identical to Y.

(XI)

In a 100 ml eggplant-shaped flask having a calcium chloride drying tube were put 1.32 grams (5 mmol) of tricyclodecanedimethanolmonomethacrylate synthesized in the first embodiment and 20 ml of dry tetrahydrofuran in argon (Ar) gas atmosphere. To the flask was also added 0.67 grams (6 mmol) of potassium tert-butoxide, and then the mixture was stirred with a teflon bar. To the mixture was further added a solution in which 1.31 grams (6 mmol) of dicarbonic acid di-tert-butyl was dissolved in 10 ml of dry tetrahydrofuran. Then, the resultant was stirred hard at an ambient temperature for 10 hours. Then, to the resultant was added 50 ml of ice and water. Then, after extraction with ethyl acetate, rinsing, cleansing with 3% sodium bicarbonate aqueous solution, and rinsing were carried out, an organic layer was dehydrated with magnesium sulfate, and then was filtrated. The solvent was removed from the filtration under reduced pressure. The residue was recrystallized to thereby obtain a target material by 1.1 grams. The yield was 60%.

IR: 1760 cm$^{-1}$ ($\nu_{C=O}$), 1720 cm$^{-1}$ ($\nu_{C=O}$), 1640 cm$^{-1}$ ($\nu_{C=C}$)

Elemental Analysis Value (Weight %) C: 69.0 (69.2) H: 8.7 (8.8)

The values in parentheses indicate calculation values calculated with $C_{21}H_{32}O_5$ whose MW is 364.484.

[Embodiment 7]: Synthesis of polymer of tricyclodecanedimethanol monomethacrylate mono-tert-butylcarbonate Tertbutoxycarbonyloxymethyltricylcodecane-methanol-methacrylate is represented by a general formula (XII) wherein Z indicates a tricyclodecane-4,8-diyl group, and m indicates a positive integer.

(XII)

In a 100 ml eggplant-shaped flask having three stop cocks and a cooling tube, 2.5 grams (6.9 mmol) of tricylcodecanedimethanol monomethacrylate mono-tert-butylcarbonate having been synthesized in the embodiment 6 was dissolved in 30 ml of dry tetrahydrofuran in argon (Ar) gas atmosphere. To the solution was added 0.033 grams (0.2 mmol) of 2,2'-azobis(isobutyronitrile), a polymerization initiator, and then the solution was heated at 60 degrees centigrade for 3 hours in an argon gas atmosphere. The resultant solution was cooled down to an ambient temperature, and then was introduced into 0.3 liter of ether. The gathered deposit was precipitated and refined once again. The deposit of precipitated polymer was gathered by filtration, and then was dried at 40 degrees centigrade under 2 mmHg for 24 hours. Thus, there was obtained 1.4 grams of polymer powder. The yield was 56%. The polystyrene equivalent molecular weight was 70000. An analyzer was model LC-9A/SPD-6A commercially available from Shimadzu Corporation, an analysis column was model GPCKF-80M commercially available from Showa Denko K.K.,and the mobile phase was tetrahydrofuran.

Elemental Analysis Value (Weight %) C: 68.9 (69.2) IR: 8.7 (8.8)

The values in parentheses indicate calculation values calculated with $(C_{21}H_{32}O_5)_n$ whose MW is 364.482.

IR(cm$^{-1}$): 1760 ($\nu_{C=O}$), 1720($\nu_{C=O}$), $v_{C=C}$ The characteristics absorption band was eliminated.

[Embodiment 8]: Synthesis of norbornanediol monomethacrylate polymer

Norbornanediol monomethacrylate is represented by a general formula (XIII) wherein A represents a norbornane-2,3-diyl group, and m indicates a positive integer.

(XIII)

Similarly to embodiment 7, norbornanediol monomethacrylate was synthesized using grams (6.9 mmol) of norbornanediolmonomethacrylate having been synthesized in the embodiment 3 in place of 2.5 grams (6.9 mmol) of tricylcodecanedimethanolmonomethacrylatemono-tert-butylcarbonate. Thus, there was obtained 0.75 grams of norbornanediolmonomethacrylate. The yield was 56%. The polystyrene equivalent molecular weight was 35000, determined by gel permeation chromatography on a Shimadzu Gel Permeation Chromatography commercially available from Showa Denko K.K.,and the mobile phase was tetrahydrofuran.

Elemental Analysis Value (Weight %) C: 67.0 (67.3) H: 8.5 (8.2)

The values in parentheses indicate calculation values calculated with $(C_{11}H_{18}O_3)_n$ whose MW is 196.246.

IR(cm$^{-1}$): 3350 ($v_{OH}$), 1725 ($v_{C=O}$), $v_{C=C}$ The characteristics absorption band was eliminated.

[Embodiment 9]: Synthesis of (2-tetrahydropyranyl)oxymethyltricylcodecanemethanolmethacrylate (2-tetrahydropyranyl)oxymethyltricylcodecanemethanolmethacrylate is represented by a general formula (XIV) wherein X and Y indicate a tetrahydropyran-2-yl group or a methacryloyl group, and X is not identical to Y.

(XIV)

Into a 200 ml flask having four openings and equipped with a thermometer, a tube for introducing nitrogen gas into the flask, and a reflux tube were put 10.0 grams (0.11 mol) of 3,4-dihydro-2H-pyran and 19.6 grams (0.1 mol) of tricyclodecane-4,8-dimethanol commercially available from Aldrich Chemical Company, Inc. (U.S.A.) with the lot number; B4, 590-9. Then, they were stirred. Then, five drops of 50% sulfuric acid were added. Thereafter, the mixture were stood at 50 degrees centigrade for 24 hours. After the mixture was cooled down to a room temperature, 3 grams of solid sodium carbonate and 10 grams of anhydrous sodium sulfate were added to the mixture. Then, the mixture was stirred for 2 hours and filtrated. The gathered filtration was disposed with 0.2 grams of hydrogenated calcium. The residue obtained by removing excessive dihydropyran by means of a rotary evaporator under reduced pressure was refined through a silica gel column to thereby obtain 18.2 grams of (2-tetrahydropyranyl)oxymethyltricylcodecanemethanol. The yield was 65%.

Elemental Analysis Value (Weight %) C: 72.5 (72.8) H: 9.9 (10.1)

The values in parentheses indicate calculation values calculated with $C_{17}H_{28}O_3$ whose MW is 280.408.

IR(cm$^{-1}$): 3350 ($v_{OH}$), 1030($v_{C-O-C}$)

Followings were put into a 100 ml flask having a silica gel drying tube, and were stirred.

(a) 11.2 grams (0.04 mol) of the thus obtained (2-tetrahydropyranyl)oxymethyltricyclodecanemethanol (b) 0.01 gram of phenothiazine (c) 20 ml of dehydrotriethylamine (d) 20 ml of dehydromethylene chloride (e) 20 ml of dehydroether While the thus obtained solution was being cooled, into the solution was slowly dropped a solution in which 4.18 grams (0.04 mmol) of methacryloyl chloride was dissolved in 5 ml of dehydromethylene chloride. The temperature of the thus obtained solution was kept to be 25 degrees centigrade or lower. After the dropping was completed, the solution was stirred at an ambient temperature for 3 hours, and then filtrated. Material obtained by filtration was sufficiently cleansed with ether. The solvent was removed from the filtration by means of a rotary evaporator under reduced pressure. The residue was dissolved in ether and then cleansed with 5% sodium carbonate solution. After an organic layer was dehydrated with anhydrous magnesium sulfate, the solvent was removed therefrom by means of a rotary evaporator under reduced pressure. After the residue was refined with silica gel column, in which ethyl acetate/n-hexane was used as an elution solvent, the residue was dried at 40 degrees centigrade under 2 mmHg for 24 hours to thereby obtain 6.2 grams of a target material, (2-tetrahydropyranyl)oxymethyltricylcodecanemethanol methacrylate. The yield was 45%.

Elemental Analysis Value (Weight %) C: 72.2 (72.4) H: 9.6 (9.3)

The values in parentheses indicate calculation values calculated with $C_{21}H_{33}O_4$ whose MW is 348.483.

IR(cm$^{-1}$): 1720 ($v_{C=O}$), 1640($v_{C=C}$)

$v_{OH}$ The characteristics absorption band was eliminated.

NMR (CDCl$_3$, internal standard material: tetramethylsilane) ppm: 0.9–2.4 (m, 23H), 3.2–3.6 (s, 4H), 3.8 (s, 2H), 4.6 (m, 1H), 5.5 (s, 1H) 6.1 (m, 1H)

[Embodiment 10]: Synthesis of polymer of (2-tetrahydropyranyl)oxymethyltricyclodecanemethanolmethacrylate (2-tetrahydropyranyl)oxymethyltricyclodecanemethanolmethacrylate is represented by a general formula (XV) wherein $Z_1$ indicates a tricyclodecane-4,8-diyl group, $Z_2$ indicates a tetrahydropyran-2-yl group, and m indicates a positive integer.

(XV)

In a 100 ml eggplant-shaped flask having three stop cocks and a cooling tube, 5.0 grams (14.3 mmol) of (2-tetrahydropyranyl)oxymethyltricyclodecanemethanolmethacrylate having been synthesized in the embodiment 9 was dissolved in 25 ml of dry tetrahydrofuran in argon (Ar) gas atmosphere. To the solution was added 0.16 grams (1 mmol) of 2,2'-azobis(isobutyronitrile), a polymerization initiator, and then the solution was heated at 60 degrees centigrade for 30 minutes in an argon gas atmosphere. The resultant solution was cooled down to an ambient temperature, and then was introduced into 0.3 liter of hexane. The gathered deposit was precipitated and refined once again. The deposit of precipitated polymer was gathered by filtration, and then was dried at 40 degrees centigrade under 2 mmHg for 24 hours. Thus, there was obtained 2.0 grams of polymer powder. The yield was 40%. The polystyrene equivalent molecular weight was 20000. An analyzer was model LC-9A/SPD-6A commercially available from Shimadzu Corporation, an analysis column was model GPCKF-80M commercially available from Showa Denko K.K., and the solvent was tetrahydrofuran.

Elemental Analysis Value (Weight %) C: 72.1 (72.4) H: 9.6 (9.3)

The values in parentheses indicate calculation values calculated with $(C_{21}H_{32}O_4)_n$ whose MW is 348.483.

IR(cm$^{-1}$): 1720 ($v_{C=O}$)

$v_{C=C}$ The characteristics absorption band was eliminated.

[Embodiment 11]

There was prepared a resist composed of the following materials A, B and C. The experiments mentioned hereinbelow were carried out under a yellow lamp.

A. 0.950 grams of the resin having been synthesized in the embodiment 5

B. 0.050 grams of cyclohexylmethyl(2-oxocyclohexyl) sulfonium trifluoromethanesulfonate This is a photo acid generator indicated with the formula (IV).

C. 4.000 grams of propyleneglycol monomethylether acetate

This is a solvent.

Figure 1:
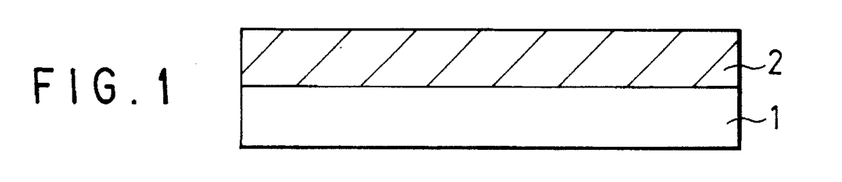
FIGS. 1, 2 and 3 are cross-sectional views of a wafer for showing steps of a method for forming a positive pattern on the wafer by using a photosensitive resin in accordance with the invention.

The mixture composed of the above mentioned materials A, B and C was filtrated with 0.2 μm teflon filter to thereby prepare a resist. On a silicon substrate having a thickness of 3 inches was applied the resist using a spin coating process, and then the resist was baked at 80 degrees centigrade for 60 seconds on a hot plate. Thus, on the substrate was formed a thin layer 2 having a thickness of 0.7 μm, as illustrated in FIG. 1. The dependency of a transmittance of the thin layer 2 on a wavelength was measured by use of a spectrophotometer for ultraviolet and visible region. The transmittance of the thin layer 2 at 193.4 nm was 71.0%. Thus, it was confirmed that the thin layer 2 had a sufficient transparency as a single layer resist.

[Embodiment 12]

Figure 2:
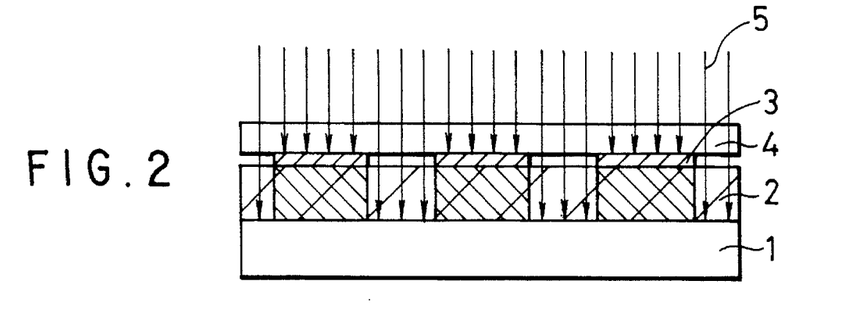
Figure 3:
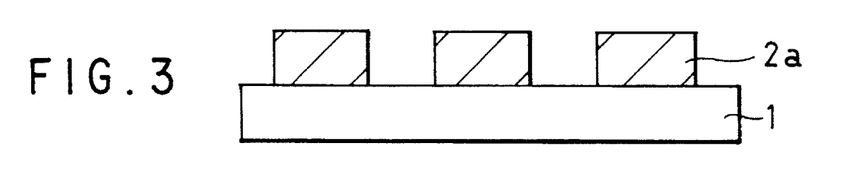
Figure 4:
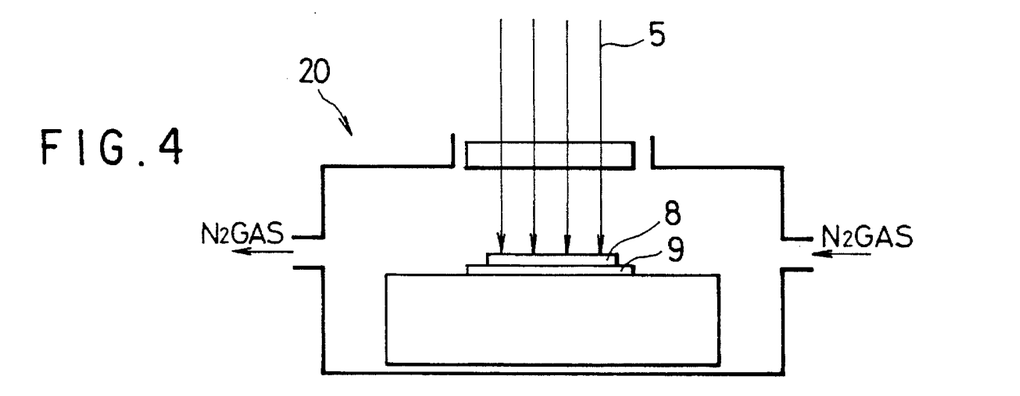
FIG. 4 is a schematic view illustrating an experimental device, set forth in the embodiments 12 and 24, for exposing a wafer to a light.

As illustrated in FIG. 4, a wafer 9 having a layer composed of the resist shown in the eleventh embodiment was placed in an exposure apparatus 20 sufficiently purged with nitrogen. On the resist layer was closely placed a mask 8 comprising a quartz plate 4 on which a pattern 3 composed of chrome is formed, and then ArF excimer laser 5 was radiated to the resist layer through the mask 8, as illustrated in FIG. 2. Shortly after that, the wafer 9 was baked on a hot plate at 90 degrees centigrade for 60 seconds, and then was developed by dipping in an alkaline developing reagent for 60 seconds. The reagent contained tetramethylammonium hydroxide at 2.3% by weight and was maintained at 23 degrees. Subsequently, the wafer was rinsed in pure water for 60 seconds. As a result, only an exposed region of the resist layer was dissolved and removed in the developing reagent, thereby there was obtained a positive type pattern 2a, as illustrated in FIG. 3. In this experiment, a resolution of 0.25 μm line and space was obtained when the exposure energy was approximately 35 mJ/cm$^2$. The resolved pattern was also observed with a scanning electron microscope (SEM) commercially available from Hitachi Co. Ltd,. under the tradename of SE-4100. The result was that unexposed region and peel of the pattern were not observed.

[Embodiment 13]: Synthesis of copolymer of (2-tetrahydropyranyl)oxymethyltricylcodecanemethanolmethacrylate and tricylcodecanedimethanolmonomethacrylate The copolymer of (2-trahydropyranyl)oxymethyltricylcodecanemethanolmethacrylate and tricylcodecanedimethanolmonomethacrylate is represented by a general formula (XVI) wherein $Z_1$ represents a tricyclodecane-4,8-diyl group, $Z_2$ represents a tetrahydropyran-2-yl group, m indicates a positive integer, and x is a variable ranging from 0 to 1 both inclusive Similarly to embodiment 10, the target copolymer was synthesized using 2.0 grams (5.7 mmol) of (2-tetrahydropyranyl)oxymethyltricyclodecanemethanolmethacrylate having been synthesized in the embodiment 9 and 2.3 grams (8.6 mmol) of tricyclodecanedimethanolmonomethacrylate synthesized in the first embodiment 1 in place of 5.0 grams (14.3 mmol) of (2-tetrahydropyranyl)oxymethyltricyclodecanemethanolmethacrylate. There was obtained 1.9 grams of the target copolymer. The polystyrene equivalent molecular weight was 25000.

[Embodiment 14]

Similarly to embodiment 11, there was prepared a resist composed of the following materials A, B and C.

A. 0.950 grams of the resin having been synthesized in the embodiment 13

B. 0.050 grams of cyclohexylmethyl(2-oxocyclohexyl) sulfonium trifluoromethanesulfonate C. 4.000 grams of propyleneglycol monomethylether acetate Then, similarly to the embodiment 12, a pattern resolution experiment was carried out with respect to the above mentioned resist. In this experiment, a resolution of 0.25 μm line and space was obtained when the exposure energy was approximately 15 mJ/cm$^2$. The resolved pattern was also observed with a scanning electron microscope (SEM). The result was that unexposed region and peel of the pattern were not observed.

[Embodiment 15]: Synthesis of (2-tetrahydropyranyl)oxymethylnorbornylalcohol (2-tetrahydropyranyl)oxymethylnorbornylalcohol is represented by a general formula (XVII) wherein each of X and Y indicates a tetrahydropyranyl group or a hydrogen atom, and X is not identical to Y.

Into a 200 ml flask having four openings and equipped with a thermometer, a tube for introducing nitrogen gas into the flask, and a reflux tube were put 10.0 grams (0.11 mol) of 3,4-dihydro-2H-pyran, 12.8 grams (100 mmol) of norbornane-2,3-diol and 50 ml of dry tetrahydrofuran. Then, they were stirred. Then, five drops of thick sulfuric acid were added. Thereafter, the mixture was allowed to stand at a room temperature for 24 hours. After the mixture was cooled down to room temperature, 3 grams of solid sodium carbonate and 10 grams of anhydrous sodium sulfate were added to the mixture. Then, the mixture was stirred for 2 hours and filtrated. The gathered filtration was disposed with 0.2 grams of hydrogenated calcium. The residue obtained by removing excessive dihydropyran by means of a rotary evaporator under reduced pressure was refined through a silica gel column, in which ethyl acetate/n-hexane was used as an elution solvent, to thereby obtain 4.0 grams of (2-tetrahydropyranyl)oxynorbornyl alcohol. The yield was 19%. The obtained (2-tetrahydropyranyl)oxynorbornyl alcohol was oily.

Elemental Analysis Value (Weight %) C: 68.0 (67.9) H: 9.8 (9.5)

The values in parentheses indicate calculation values calculated with $C_{12}H_{20}O_3$ whose MW is 212.289.

IR(cm$^{-1}$): 3350 ($v_{OH}$), 1030($v_{C-O-C}$)

[Embodiment 16]: Synthesis of (2-tetrahydropyranyl)oxynorbornylalcohol acrylate (2-tetrahydropyranyl)oxynorbornylalcohol acrylate is represented by a general formula (XVIII) wherein each of X and Y indicates a tetrahydropyranyl group or an acryloyl group, and X is not identical to Y.

(XVIII)

The followings was put into a 100 ml flask having a silica gel drying tube, and stirred.

(a) 8.4 grams (0.04 mol) of (2-tetrahydropyranyl)oxynorbornylalcohol having been synthesized in the embodiment 15

(b) 0.01 gram of phenothiazine (c) 20 ml of dehydrotriethylamine (d) 20 ml of dehydromethylene chloride (e) 20 ml of dehydroether While the thus obtained solution was being cooled, 3.62 grams (0.04 mmol) of acryloyl chloride dissolved in 5 ml of dehydromethylene chloride was slowly dropped into the solution. The temperature of the thus obtained solution was kept to be 25 degrees centigrade or lower. After the dropping was completed, the solution was stirred at an ambient temperature for 3 hours, and then filtrated. Material obtained by filtration was sufficiently cleansed with ether. The solvent was removed from the filtration by means of a rotary evaporator under reduced pressure. The residue was dissolved in ether and then cleansed with 5% sodium carbonate solution. After an organic layer was dehydrated with anhydrous magnesium sulfate, the solvent was removed therefrom by means of a rotary evaporator under reduced pressure. After the residue was refined with silica gel chromato, in which ethyl acetate/n-hexane was used as an elution solvent, the residue was gathered and then dried at a room temperature under reduced pressure for 24 hours to thereby obtain 3.4 grams of a target material, (2-tetrahydropyranyl)oxynorbornylalcoholacrylate. The yield was 32%. The obtained (2-tetrahydropyranyl)oxynorbornylalcohol acrylate was oily.

Elemental Analysis Value (Weight %) C: 68.4 (68.0) H: 8.3 (8.0)

The values in parentheses indicate calculation values calculated with $C_{16}H_{22}O_4$ whose MW is 266.350.

IR(cm$^{-1}$): 1720 ($v_{C=O}$), 1640 ($v_{C=C}$), 1030 ($v_{C-O-C}$)

$v_{OH}$ The characteristics absorption band was eliminated.

[Embodiment 17]: Synthesis of polymer of (2-tetrahydropyranyl)oxynorbornylalcoholacrylate (2-tetrahydropyranyl)oxynorbornylalcoholacrylate is represented by a general formula (XIX) wherein $Z_1$ indicates a norbornanediyl group, $Z_2$ indicates a tetrahydropyranyl group, and m indicates a positive integer.

In a 100 ml eggplant-shaped flask having three stop cocks and a cooling tube, 3.81 grams (14.3 mmol) of (2-tetrahydropyranyl)oxymethylnorbornyl alcohol acrylate synthesized according to the sixteenth embodiment was dissolved in 25 ml of dry tetrahydrofuran in argon (Ar) gas atmosphere. To the solution was added 0.16 grams (1 mmol) of 2,2'-azobis(isobutyronitrile), a polymerization initiator, and then the solution was heated at 60 degrees centigrade for 30 minutes in an argon gas atmosphere. The resultant solution was cooled down to an ambient temperature, and then was introduced into 0.3 liter of hexane. The gathered deposit was precipitated and refined once again. The deposit of precipitated polymer was gathered by filtration, and then was dried at 40 degrees centigrade under 2 mmHg for 24 hours. Thus, there was obtained 1.9 grams of polymer powder. The yield was 50%. The polystyrene equivalent molecular weight was 27000.

Elemental Analysis Value (Weight %) C: 68.3 (68.0), H: 8.2 (8.0)

The values in parentheses indicate calculation values calculated with $(C_{18}H_{22}O_4)_n$ whose MW is 266.350.

IR(cm$^{-1}$): 1720 ($v_{C=O}$), 1030 ($v_{C-O-C}$)

$v_{C=C}$ The characteristics absorption band was eliminated.

[Embodiment 18]: Synthesis of copolymer of (2-tetrahydropyranyl)methacrylate and tricylcodecanedimethanolmonomethacrylate The copolymer of (2-tetrahydropyranyl)methacrylate and tricylcodecanedimethanolmonomethacrylate is represented by a general formula (XX) wherein $Z_1$ represents a tricyclodecane-4,8-diyl group, $Z_2$ represents a tetrahydropyran-2-yl group, m indicates a positive integer, and x is a variable ranging from 0 to 1 both inclusive.

Similarly to embodiment 13, the target copolymer was synthesized using 0.52 grams (3.1 mmol) of tetrahydropyranylmethacrylate in place of 2.0 grams (5.7 mmol) of (2-tetrahydropyranyl)oxymethyl-tricyclodecanemethanolmethacrylate. Tetrahydropyranylmethacrylate was synthesized in accordance with a known method such as the method suggested in Chemistry Material, 1991, Vol. 3 (6), pages 103–1040 by G. N. Taylor et al.. There was obtained 1.2 grams of the target copolymer. A copolymerization ratio was measured by means of $^1$H-NMR, resulting that x was 35 and that the copolymerization ratio was equal to a mixture ratio of starting materials. The polystyrene equivalent molecular weight was 22300.

[Embodiment 19]

There was prepared a resist composed of the following materials A, B and C. The experiments mentioned hereinbelow were carried out under a yellow lamp.

A. 0.995 grams of the resin having been synthesized in the embodiment 18

B. 0.005 grams of cyclohexylmethyl(2-oxocyclohexyl) sulfonium trifluoromethanesulfonate This is a photo acid generator indicated with the formula (IV).

C. 4.000 grams of ethyleneglycol monomethylether

This is a solvent.

The mixture composed of the above mentioned materials A, B and C was filtrated with 0.2 μm teflon filter to thereby prepare a resist. On a silicon substrate having a thickness of 3 inches was applied the thus prepared resist with spin coating process, and then the resist was baked at 80 degrees centigrade for 60 seconds on a hot plate. Thus, on the substrate was formed a thin layer having a thickness of 0.7 μm. The dependency of a transmittance of the thin layer on a wavelength was measured by use of a spectrophotometer for ultraviolet and visible region. The transmittance of the thin layer at 193.4 nm was 68%. Thus, it was confirmed that the thin layer 2 had a sufficient transparency as a single layer resist.

[Embodiment 20]: Synthesis of (1-(ethoxy)ethyl)oxymethyltricyclodecanemethanolmethacrylate (1-(ethoxy)ethyl)oxymethyltricyclodecanemethanolmethacrylate is represented by a general formula (XXI) wherein each of X and Y indicates a 1-(ethoxy)ethyl group or a methacryloyl group, and X is not identical to Y.

(XXI)

In a 200 ml flask having four openings and equipped with a thermometer, a tube for introducing nitrogen gas into the flask, and a reflux tube, there were mixed 7.9 grams (0.11 mol) of ethylvinylether, 19.6 grams (0.1 mol) of tricyclodecane-4,8-dimethanol, 5 mmol of p-toluene sulfonic acid and 100 ml of methylene chloride. Thereafter, the mixture were stood at a room temperature for 3 hours. After adding 200 ml of diethylether to the mixture, the mixture was washed with 5% sodium carbonate aqueous solution, saturated salt aqueous solution and pure water in turn. Then, organic layer was gathered and alehydrated by sodium sulfate anhydride. Then, the solvent was removed. The residue was refined through a silica gel column, in which ethyl acetate/n-hexane was used as an elution solvent, to thereby obtain 12.0 grams of (1-(ethoxy)ethyl)oxymethyltricyclodecanemethanol. The yield was 45%.

IR(cm$^{-1}$): 3350 ($v_{OH}$), 1030 ($v_{C-O-C}$)

Among the thus obtained 12.0 grams of (1-(ethoxy)ethyl)oxymethyltricyclodecanemethanol, 10.7 grams of it was replaced with (2-tetrahydropyranyl)oxymethytricyclodecanemethanol synthesized according to the ninth embodiment. Then, the solution was refined through a silica gel column, in which ethyl acetate/n-hexane was used as an elution solvent, with other conditions remaining unchanged, to thereby obtain 5.4 grams of (1-(ethoxy)ethyl)oxymethyltricyclodecanemethanolmethacrylate. The yield was 40%. The obtained (1-(ethoxy)ethyl)oxymethyltricyclodecanemethanolmethacrylate was oily.

Elemental Analysis Value (Weight %) C: 71.5 (71.4), H: 9.8 (9.6)

The values in parentheses indicate calculation values calculated with $C_{20}H_{32}O_4$ whose MW is 336.472.

IR(cm$^{-1}$): 1720 ($v_{C=O}$), 1640 ($v_{C=C}$), 1030 ($v_{C-O-C}$)

$v_{C=C}$ The characteristics absorption band was eliminated.

[Embodiment 21]: Synthesis of (1-(butoxy)ethyl)oxymethyltricyclodecanemethanolmethacrylate (1-(butoxy)ethyl)oxymethyltricyclodecanemethanolmethacrylate is represented by a general formula (XXII) wherein each of X and Y indicates a 1-(butoxy)ethyl group or a methacryloyl group, and X is not identical to Y.

(XXII)

In a 200 ml flask having four openings and equipped with a thermometer, a tube for introducing nitrogen gas into the flask, and a reflux tube, there were mixed 11.0 grams (0.11 mol) of n-butylvinylether, 19.6 grams (0.1 mol) of tricyclodecane-4,8-dimethanol, 5 mmol of p-toluene sulfonic acid and 100 ml of methylene chloride. Thereafter, the mixture was allowed to stand at room temperature for 3 hours. After adding 200 ml of diethylether to the mixture, the mixture was washed with 5% sodium carbonate aqueous solution, saturated salt aqueous solution and pure water in turn. Then, organic layer was gathered and dehydrated by sodium sulfate anhydride. Then, the solvent was removed. The residue was refined through a silica gel column to thereby obtain 13.9 grams of (1-(butoxy)ethyl)oxymethyltricyclodecanemethanol. The yield was 47%.

IR(cm$^{-1}$): 3350 ($v_{OH}$), 1030 ($v_{C-O-C}$)

Among the thus obtained 13.9 grams of (1-(butoxy)ethyl)oxymethyltricyclodecanemethanol, 11.9 grams of it was replaced with (2-tetrahydropyranyl)oxymethyltricyclodecanemethanol synthesized according to the ninth embodiment. Then, the solution was refined through a silica gel column, in which ethyl acetate/n-hexane was used as an elution solvent, with other conditions remaining unchanged, to thereby obtain 6.3 grams of (1-(butoxy)ethyl)oxymethyltricyclodecanemethanolmethacrylate. The yield was 43%. The obtained (1-(butoxy)ethyl)oxymethyltricyclodecanemethanolmethacrylate was oily.

Elemental Analysis Value (Weight %) C: 72.3 (72.5), H: 9.9 (9.9)

The values in parentheses indicate calculation values calculated with $C_{20}H_{32}O_4$ whose MW is 364.526.

IR(cm$^{-1}$): 1720 ($v_{C=O}$), 1640 ($v_{C=C}$), 1030 ($v_{C-O-C}$)

$v_{C=C}$ The characteristics absorption band was eliminated.

[Embodiment 22]: Synthesis of quaterpolymer of (1-(ethoxy)ethyl)oxymethyltricyclodecanemethanolmethacrylate, (2-tetrahydropyranyl)methacrylate, tricyclodecanedimethanolmonomethacrylate and methacrylic acid Quaterpolymer of (1-(ethoxy)ethyl)oxymethyltricyclodecanemethanolmethacrylate, (2-tetrahydropyranyl)methacrylate, tricyclodecanedimethanolmonomethacrylate and methacrylic acid is represented by a general formula (XXIII) wherein $Z_1$ indicates a tricyclodecane-4,8-diyl group, $Z_2$ indicates a 1-(ethoxy)ethyl group, $Z_3$ indicates a tetrahydropyran-2-yl group, m indicates a positive integer, and a total of "a", "b", "c" and "d" is one (1), that is, a+b+c+d=1.

In a 500 ml eggplant-shaped flask having three stop cocks and a cooling tube, the following A to D were dissolved in 200 ml of dry tetrahydrofuran in argon (Ar) gas atmosphere:
A. 34.3 grams (102 mmol) of (1-(ethoxy)ethyl)oxymethyl-tricyclodecanemethanolmethacrylate synthesized according to the twentieth embodiment;
B. 31.5 grams (119 mmol) of tricyclodecanedimethanol-monomethacrylate which was synthesized in the embodiment 1;
C. 11.58 grams (38 mmol) of tetrahydropyranylmethacrylate;
D. 4.41 grams (51 mmol) of methacrylic acid.

To the solution was added 1.92 grams (12 mmol) of 2,2'-azobis(isobutyronitrile), a polymerization initiator, and then the solution was heated at 60 degrees centigrade for 30 minutes in an argon gas atmosphere. The resultant solution was cooled down to an ambient temperature, and then was introduced into 0.7 liter of hexane. The gathered deposit was precipitated and refined twice. The deposit of precipitated polymer was gathered by filtration, and then was dried at 40 degrees centigrade under 2 mmHg for 24 hours. Thus, there was obtained 35.0 grams of polymer powder. The yield was 40%. The polystyrene equivalent molecular weight was 18700. The copolymerization ratio was identical to a mixture ratio of raw materials, namely, "a"=0.38, "b"=0.33, "c"=0.12 and "d"=0.17.

[Embodiment 23]

There was prepared a resist composed of the following materials A, B and C. The experiments mentioned hereinbelow were carried out under a yellow lamp.

A. 0.995 grams of the resin having been synthesized in the embodiment 22

B. 0.005 grams of cyclohexy-methyl(2-oxocyclohexyl-)sulfonium trifluoromethanesulfonate This is a photo acid generator indicated with the formula (IV).

C. 4.000 grams of diethylene glycol dimethyl ether
This is a solvent.

The mixture composed of the above mentioned materials A, B and C was filtrated with 0.2 μm teflon filter to thereby prepare a resist. On a silicon substrate having a thickness of 3 inches was applied the thus prepared resist with spin coating process, and then the resist was baked at 80 degrees centigrade for 60 seconds on a hot plate. Thus, on the substrate was formed a thin layer having a thickness of 0.7 μm. The dependency of a transmittance of the thin layer on a wavelength was measured by use of a spectrophotometer for ultraviolet and visible region. The transmittance of the thin layer at 193.4 nm was 65%. Thus, it was confirmed that the thin layer had a sufficient transparency as a single layer resist.

[Embodiment 24]

As illustrated in FIG. 4, a wafer 9 having a layer composed of the resist shown in embodiment 19 was placed in an exposure apparatus 20 sufficiently purged with nitrogen. On the resist layer was closely placed a mask 8 comprising a quartz plate 4 on which a pattern 3 composed of chrome is formed, and then ArF excimer laser 5 was radiated to the resist layer through the mask 8, as illustrated in FIG. 2. Shortly after that, the wafer 9 was baked on a hot plate at 80 degrees centigrade for 60 seconds, and then was developed by dipping in an alkaline developing reagent for 60 seconds. The reagent contained tetramethylammonium hydroxide at 2.38% by weight and was maintained at 23 degrees centigrade. Subsequently, the wafer was rinsed in pure water for 60 seconds. As a result, only an exposed region of the resist layer was dissolved and removed in the developing reagent, thereby there was obtained a positive type pattern 2a, as illustrated in FIG. 3. In this experiment, a resolution of 0.25 μm line and space was obtained when the exposure energy was approximately 43 mJ/cm$^2$. The resolved pattern was also observed with a scanning electron microscope (SEM) commercially available from Hitachi Co. Ltd,. under the tradename of SE-4100. The result was that unexposed region and peel of the pattern were not observed.

Similarly, a pattern resolution experiment was carried out using a resist shown in embodiment 23. The result of the experiment was that a resolution of 0.3 μm line and space was obtained when the exposure energy was approximately 30 mJ/cm$^2$.

As having been explained so far in connection with the preferred embodiments, the photosensitive resin in accordance with the invention, which contains a novel polymer obtained by polymerizing a novel monomer which is also obtained in accordance with the invention, has a high transparency to far ultraviolet (FUV) radiation region having a wavelength of 220 nm or shorter, and also has a high sensitivity and resolution to FUV exposure light. Thus, the photosensitive resin in accordance with the invention is suitable for a photoresist which uses far ultraviolet radiation, in particular ArF excimer laser having a wavelength of 220 nm or shorter, as exposure light. In addition, the photosensitive resin in accordance with the invention makes it possible to form a minute pattern necessary for manufacturing a semiconductor element.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A photosensitive resin comprising a resin and a photo acid generator, said resin including a polymer represented by formula (II) wherein $R_1$ and $R_6$ are independently selected from the group consisting of a hydrogen atom, a tert-butoxycarbonyl group, a tetrahydrofuran-2-yl group, a 4-methoxytetrahydropyranyl group, a 1-ethoxyethyl group, a 1-butoxyethyl group and a 1-propoxymethyl group, $R_2$ and $R_4$ each represents a hydrocarbon residue including a bridged hydrocarbon group and having a carbon number ranging from 7 to 12, both inclusive, $R_3, R_5, R_7$ and $R_8$ each represent a hydrogen atom or methyl group, "a" is a variable ranging from 0 to 0.9 both inclusive, "b" is a variable ranging from 0 to 0.9 both inclusive, "c" is a variable ranging from 0 to 0.7 both inclusive, "d" is a variable ranging from 0 to 0.5 both inclusive, the sum of "a", "b", "c" and "d" is one, provided that both "a" and "b" are not 0, and wherein n represents a positive integer ranging from 10 to 500 both inclusive, said resin being included in said photosensitive resin by weight percent in the range from 75 to 99.8 both inclusive, and said photo acid generator being included in said photosensitive resin by weight percent in the range from 0.2 to 25 both inclusive.

2. The photosensitive resin as recited in claim 1, wherein said photo acid generator generates an acid under a light having a wavelength equal to or less than 300 nm.

3. The photosensitive resin as recited in claim 1, wherein said photo acid generator generates an acid under a light having a wavelength equal to or less than 220 nm.

4. The photosensitive resin as recited in claim 1, wherein said photo acid generator comprises a plurality of kinds of photo acid generators.

5. The photosensitive resin as recited in claim 1, wherein said photo acid generator is selected from a group consisting of triphenylsulfonium salt derivatives, onium salts, 2,6-dinitrobenzyl ester, 1,2,3-tri(methanesulfonyloxy)benzene and sulfosuccinimide.

6. The photosensitive resin as recited in claim 1, wherein said photo acid generator has a general formula (IV) wherein $R_9$ and $R_{10}$ are one of straight-chain, branching and cyclic alkyl groups, and $R_{11}$ is one of straight-chain, branching and cyclic alkyl groups, a 2-oxocyclic alkyl group, 2-oxostraight-chain and branching alkyl groups, and Y— represents a twin ion 7. The photosensitive resin as recited in claim 1, wherein said photo acid generator has a general formula (V) wherein $R_{12}$ and $R_{13}$ are one of a hydrogen and straight-chain, branching and cyclic alkyl groups, and $R_{14}$ is one of a hydrogen, straight-chain, branching and cyclic alkyl groups and a haloalkyl group, 8. The photosensitive resin as recited in claim 6, wherein said photo acid generator is selected from a group consisting essentially of cyclohexylmethyl(2-oxocyclohexyl)sulfonium trifluoromethanesulfonate, dicyclohexyl(2-oxocyclohexyl)sulfonium trifluoromethanesulfonate, 2-cyclohexylsulfonylcyclohexanone, dimethyl(2-oxocyclohexyl) sulfonium trifluoromethanesulfonate, triphenylsulfonium trifluoromethanesulfonate, diphenyliodonium and trifluoromethanesulfonate.

9. The photosensitive resin as recited in claim 7, wherein said photo acid generator is selected from a group consisting essentially of N-hydroxysuccinimide trifluoromethanesulfonate.

10. The photosensitive resin as recited in claim 1, wherein said photo acid generator is contained by weight percent in the range from 0.2 to 25 both inclusive.

11. The photosensitive resin as recited in claim 10, wherein said photo acid generator is contained by weight percent in the range from 1 to 15 both inclusive.

* * * * *